United States Patent [19]
Hughes

[11] Patent Number: 5,820,553
[45] Date of Patent: Oct. 13, 1998

[54] IDENTIFICATION SYSTEM AND METHOD FOR RADIATION THERAPY

[75] Inventor: John H. Hughes, Martinez, Calif.

[73] Assignee: Siemens Medical Systems, Inc., Iselin, N.J.

[21] Appl. No.: 708,065

[22] Filed: Aug. 16, 1996

[51] Int. Cl.$^6$ ........................................... A61N 5/00
[52] U.S. Cl. .................... 600/426; 600/1; 600/427; 378/65
[58] Field of Search ................... 128/653.1, 654, 128/659, 897; 378/65, 68, 69, 162, 165, 204, 205, 208, 209; 250/491.1, 492.1; 600/1–3, 431, 436, 426, 427

[56] References Cited

U.S. PATENT DOCUMENTS

| | | |
|---|---|---|
| 4,638,814 | 1/1987 | Spanswick . |
| 4,791,934 | 12/1988 | Brunnett .................................. 600/429 |
| 4,905,267 | 2/1990 | Miller et al. ............................. 378/208 |
| 5,117,829 | 6/1992 | Miller et al. ........................... 128/653.1 |
| 5,315,630 | 5/1994 | Sturm et al. ............................... 378/65 |
| 5,446,548 | 8/1995 | Gerig et al. ............................. 356/375 |
| 5,622,187 | 4/1997 | Carol ....................................... 128/897 |
| 5,630,422 | 5/1997 | Zanakis ................................... 600/473 |

*Primary Examiner*—Ruth S. Smith

[57] ABSTRACT

A system and method for identifying and processing individual patients among a set of patients includes storing position data representative of patient-unique arrangements of targets that are affixed to the patients for aligning a therapeutic radiation beam. Subsequent to the recording of the position data, a particular patient and/or the medical information of the particular patient can be identified by reimaging the targets or substitute targets on the particular patient to detect a correlation between the image data and the stored position data. The correlation may be used to register a patient, track the location of the patient within a multi-station facility, or facilitate treatment setup, such as beam-to-patient alignment, radiation configuration, and beam control.

19 Claims, 3 Drawing Sheets

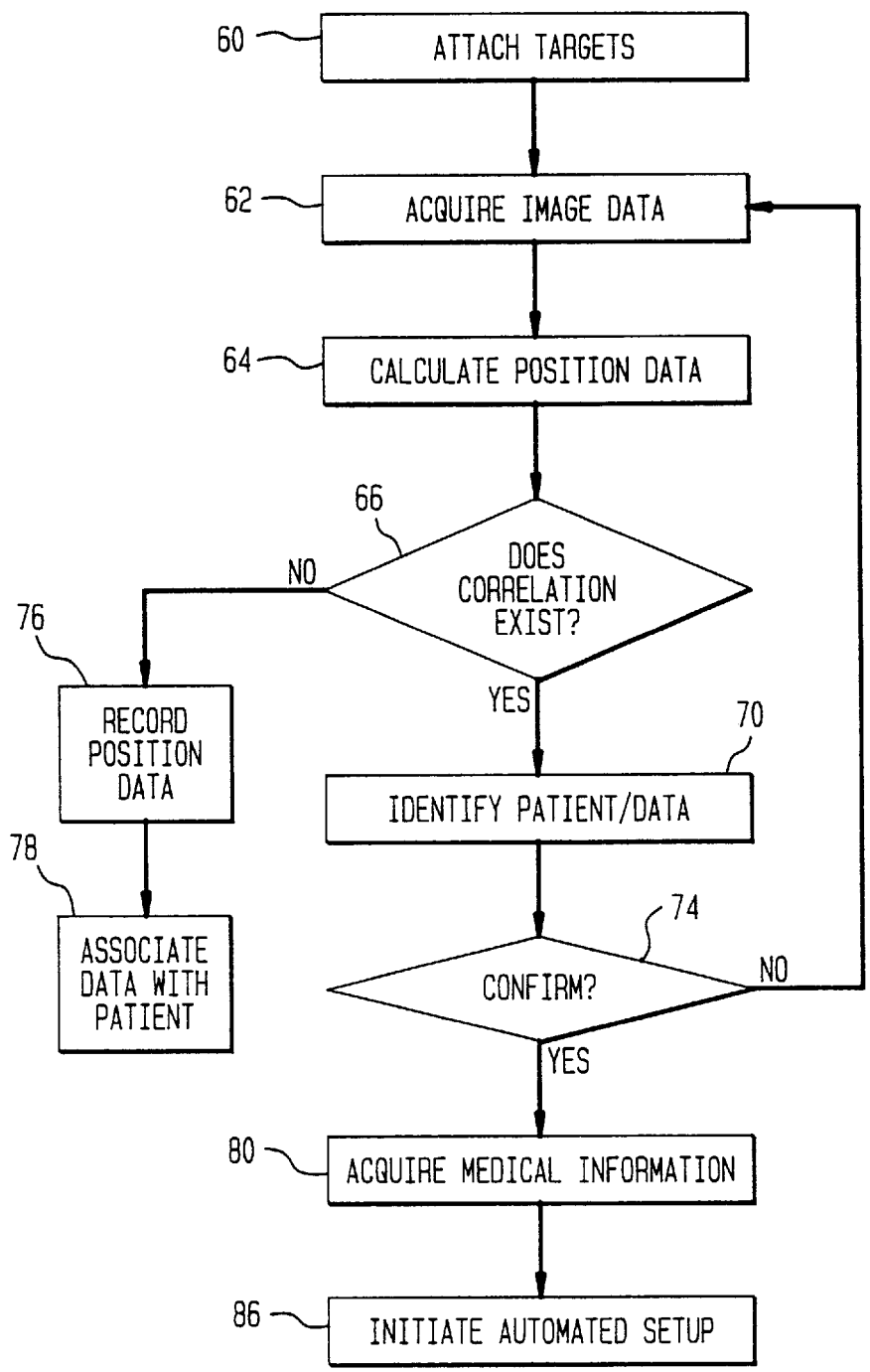

IDENTIFICATION SYSTEM AND METHOD FOR RADIATION THERAPY

BACKGROUND OF THE INVENTION

The invention relates generally to radiation therapy and more particularly to systems and methods for automating the identification of medical patients and/or the identification of medical information with a particular patient.

DESCRIPTION OF THE RELATED ART

Radiation-emitting devices are generally known and used, for instance, as radiation therapy devices for the treatment of patients. A radiation therapy device typically includes a gantry which can be swiveled about a horizontal axis of rotation in the course of a therapeutic session. A linear accelerator is located in the gantry for generating a high-energy radiation beam. The high-energy radiation beam can be electron radiation or photon (X-ray) radiation. During treatment, the radiation beam is trained on a zone of patient lying in the isocenter of the gantry rotation. Typically, the patient is rested on a rotatable table. The combination of movements of the gantry and the table permits movement of the patient about mutually perpendicular X, Y and Z axes. These rotations are sometimes referred to by the terms "tilt," "roll" and "yaw," respectively.

In radiation therapy, the radiation beam is directed at diseased tissue, but with a goal of minimizing any adverse effect upon adjacent healthy tissue. For this reason, the relative positions of the patient and the source of radiation are important. U.S. Pat. No. 5,446,548 to Gerig et al., which is assigned to the assignee of the present invention, describes a sensing system for monitoring patient position for radiation therapy. The sensing system can report variations in patient setup from day to day, as well as motion during an individual session. Targets are affixed to a patient positioned on the table under the gantry. The targets may be a retroreflective material on one side of a flat tape having pressure-sensitive adhesive on the opposite side. Typically, three to five targets are affixed to the patient. At least one light source, such as a laser, provides radiation that impinges the targets. Cameras are focused at the table, and the outputs of the cameras are applied to image acquisition and processing boards to determine the positions of the targets in three-dimensional space. Within a single session, data representative of the positions of the targets are stored and then compared with a subsequent determination of the positions of the same targets, so that any movement of the patient can be detected. A display may be used to graphically represent any differences in the position of the targets, i.e. the patient, so that the operator is alerted to any changes. The same techniques may be used for day-to-day positioning. The operator may request access to reference data that include the coordinates of each target as measured in a prior session. These reference data are compared to coordinates ("setup data") of each target on the patient as measured immediately prior to therapy, so that the operator can determine and adjust the patient's position before radiation is delivered.

The system of Gerig et al. reduces the setup time for radiation therapy by storing data that can be requested by an operator of the radiation device, with the requested information then being used by the operator to duplicate target coordinates. Nevertheless, the limitation to patient throughput may only be forty patients per day. As a result, demand for the radiation therapy device often exceeds the capacity of the device.

What is needed is a system and method that provide further increases to patient throughput for a radiation therapy device by facilitating one or both of the administrative processing and the setup processing of patients and the device.

SUMMARY OF THE INVENTION

A system for identifying a medical patient within a set of patients who are scheduled for radiation therapy includes memory for storing position data representative of arrangements of targets that are fixed relative to the patients. Originally, a number of targets are affixed to a patient for the purpose of positioning the patient relative to a source of radiation. However, according to the invention, the target arrangement on the patient is unique to that patient, and is used as an identification. The system includes an imaging scheme, such as two appropriately positioned cameras, for generating image data that are responsive to positions of the targets on a particular patient. In the preferred embodiment, the image data are used to determine the three-dimensional positions of the individual targets. Processing circuitry compares the determined positions of the targets on the particular patient to the position data stored in memory in order to detect a correlation. Thus, the arrangement of targets may be used as an identifier in a digital approach.

In one embodiment, the identification based upon target positions is used to register patients for one session of a multi-session radiation treatment plan. In a related embodiment, the identification is used to track a patient in a multi-station medical environment, such as a clinic in which patients progress through testing stations before treatment. In the preferred embodiment, the setup information for a particular patient is identified based upon the target positions, so that the setup information for a particular session is downloaded and used to expedite the setup process. In this preferred embodiment, prescribed parameters are automatically established, such as beam-to-patient alignment, geometric radiation pattern configuration, and radiation intensity and exposure time settings. In addition to or as a substitute for the setup information, other medical information regarding the patient may be identified using the invention.

BRIEF DESCRIPTION OF THE DRAWINGS

FIG. 3 is a process flow view of steps for utilizing the system of FIG. 1 in accordance with the invention.

DETAILED DESCRIPTION

Figure 1:
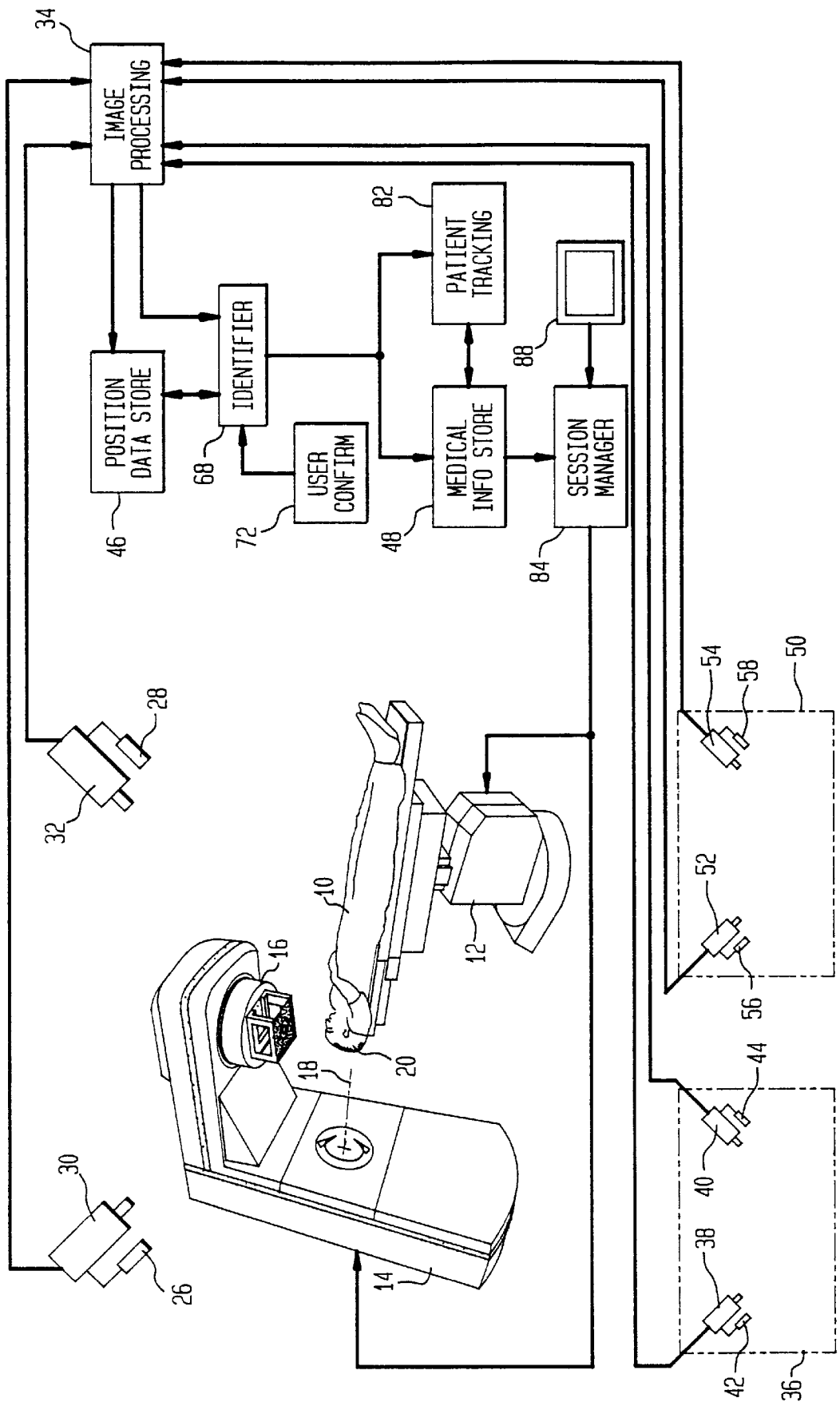
FIG. 1 is a block diagram of a system for identifying a medical patient in accordance with the invention.

As will be described fully below, the system of FIG. 1 can be utilized for a number of purposes, including patient registration, patient tracking, radiation-to-patient alignment and alignment tracking. Some of the alignment features are described in U.S. Pat. No. 5,446,548 to Gerig et al., which is assigned to the assignee of the present invention, but the patent does not describe the use of targets to identify a patient or to identify medical information that is specific to a particular patient.

A patient 10 is shown as resting on a table 12 under a gantry 14 of a radiation therapy machine. A radiation beam is directed from the gantry toward the patient. The radiation beam is generated by a linear accelerator within the gantry and is emitted from a collimator 16. The radiation beam may be electron radiation or photon radiation, i.e. X-ray radiation. The gantry 14 is well known in the art.

The combination of the table 12 and the gantry 14 permits realignment of the patient to the radiation beam along X, Y and Z axes. Patient movement is sometimes specified using the terminology tilt, roll and yaw, which are defined as rotations about axes parallel to the principal X, Y and Z axes, respectively. The gantry 14 rotates about the horizontal axis 18. The table can be moved to correct for tilt and roll. The table is conventionally used in clinical radiation systems, but other devices for aligning a patient relative to a radiation beam may be utilized.

In addition to adjustments of the positions of the table 12 and the gantry 14, there are adjustment mechanisms directly associated with the collimator 16. These adjustment mechanisms allow the radiation beam to be geometrically shaped to the requirements of specific patients. Multi-leaf collimators may have twenty-seven sets of plates that are individually manipulated to establish a desired radiation pattern. Moreover, the collimator is typically rotatable, so that the established pattern rotates relative to the patient. As a result, for a particular patient, the radiation field can be specifically suited to irradiate diseased tissue, while minimizing any adverse effect upon adjacent healthy tissue.

Beam parameters are also variable. Each patient is associated with a treatment plan that identifies prescribed radiation energy, exposure time, and other treatment parameters, as well as the desired radiation pattern. In the preferred embodiment of the invention, targets 20 are employed to identify the patient 10, to initiate automatic access to the patient's treatment plan, and to initiate the setup sequence for executing the prescribed treatment plan.

An arrangement of targets 20 is shown as being affixed to the head of the patient 10. The body portion of the patient to which the targets are affixed is not critical. For example, if the patient is to receive radiation therapy to treat diseased brain tissue, the targets may be affixed to the chest of the patient, if it is determined that the proper alignment can still be reproduced from one therapy session to the next. It is also possible to affix the targets to a device that is then affixed to the patient, but this may introduce some alignment inaccuracies. Therefore, the preferred embodiment includes affixing the targets directly to the patient.

In the preferred embodiment, each target is a piece of tape having retroreflective material on a first side and a pressure-sensitive material on the opposite side. Retroreflective materials are well known in the art and are commercially available. Preferably, at least three targets are affixed to the patient 10. The arrangement 20 of targets on the patient 10 is unique to that patient. That is, the target positioning in three-dimensional space is not duplicated by target positioning on any other patient who is treated using the radiation system.

Figure 2:
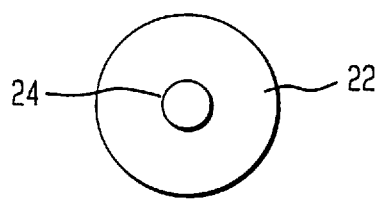
FIG. 2 is a front view of one of the targets of FIG. 1.

Referring now to FIG. 2, a target 22 may have an annular configuration, but this is not critical. An acceptable outside diameter for the target is 12.5 mm. As previously noted, the target may have a pressure-sensitive adhesive back to ensure that the target does not move during a session of a treatment plan. Often, the targets are removed after each session and replaced the following day, but a single target may be used for a number of sessions.

At the center of the target 22 is a substantially circular hole 24. An acceptable diameter of the hole is 2.0 mm. The hole may be used by an operator/techologist to locate targets in the identical position on a patient from day to day. This is done by visually locating a mark placed on the patient during a therapy simulation process. During the simulation process the region of the patient's skin that is aligned with the hole 24 may be marked with a tattoo. Then, for subsequent therapy sessions, the tattoo marks are visually aligned with the holes in the target. The shape of the center hole is not critical. In fact, the function served by the hole may be achieved by providing an area of the target that is sufficiently thin to permit visual sighting of a marker through the material.

In the preferred embodiment, the top layer of the target 22 is a retroreflective material. Phosphorescent or fluorescent materials may be substituted. Such materials are easily distinguished from the skin of the patient, so that target imaging data are more reliable.

Referring again to FIG. 1, light sources 26 and 28 provide radiation which impinges upon the arrangement of targets 20. In the preferred embodiment, the light sources produce infrared radiation. The infrared radiation enables the system to more reliably distinguish light reflected from the targets, as opposed to background radiation that may be present in the therapy room under ambient lighting conditions. The light sources may be infrared lasers, with the infrared radiation being spread by lenses, not shown. The use of laser light sources provides the advantage that the spectral bandwidth of the radiation is narrow, providing a further reduction in background interference.

A pair of cameras 30 and 32 are directed at the patient 10. While not critical, the cameras may be charged coupled device (CCD) cameras equipped with infrared filters to reduce the susceptibility of the cameras to background radiation.

The outputs of the cameras 30 and 32 are applied to an image processing circuit 34. The image processing circuit may include an acquisition board purchased from Matrox Corporation as IM-1280. Image processing may also include a vision-based coordinate measurement (VCM) system as used to determine target positioning in three-dimensional space. In the preferred embodiment, the VCM system is a software package which can be integrated with commercially available solid-state cameras, image acquisition and processing boards, and computer hardware. The VCM system combines principles of stereo vision, photogrammetry and knowledge-based techniques to provide precise coordinate and dimension measurements of objects. The VCM system has been used with other medical applications, including the system described in the Gerig et al. patent. The two cameras 30 and 32 and the three-dimensional image processing circuit 34 are calibrated such that the frame of reference is coincident with the therapy system, with an isocenter defined as 0,0,0. The coordinate system is defined such that the X axis lies in a horizontal plane perpendicular to the gantry axis 18 of rotation and passes through the isocenter, the Y axis is parallel to the gantry axis of rotation and passes through the isocenter, and the Z axis is mutually perpendicular to the other two axes and defines patient height.

In the preferred embodiment, position data regarding the arrangement 20 of targets are acquired prior to a session in which therapeutic radiation is applied to the patient 10. For example, the position data may be acquired during a simulation session that takes place at a different station 36 of a clinic or other medical environment. The station 36 may include a simulator, i.e., a radiographic imaging system operated in the diagnostic X-ray range to direct a radiation beam in the same alignment that is determined to be the desired alignment for therapeutic radiation. Thus, the simulation session is used in the formulation of a treatment plan for defining parameters such as exposure time, dose, distance, geometry and direction. The station 36 includes a pair of cameras 38 and 40 and light sources 42 and 44 identical to those that are directed at the patient 10 in FIG. 1.

The outputs of the cameras 38 and 40 are inputs to the image processing circuit 34. The image processing determines the position data for a particular patient and stores the position data within memory 46. The memory 46 includes target position data for the patient 10 and for other patients who are scheduled or have been scheduled to receive radiation therapy from the gantry 14. In the preferred embodiment, a second memory 48 stores medical information that includes the treatment plans for the various patients. This second memory may also be used to store the medical histories of the patients.

If the position data regarding the target positions for the individual patients are acquired using the cameras 38 and 40 and the station 36, the position data are nevertheless accessible for patient processing at other stations in a clinic. For example, a third station 50 may be a registration room for arriving patients. If a patient arrives for a session, targets are attached to the patient in the same arrangement as any previous sessions. Cameras 52 and 54 may be used to image the targets in order to identify the patient and automatically access medical information stored within the second memory 48. The patient then waits within a waiting area of the third station 50. Light sources 56 and 58 are included within the third station, but are not critical. The light sources are preferably identical to the light sources 26 and 28 that are used to enhance imaging by the cameras 30 and 32.

Referring now to FIGS. 1 and 3, in the first step 60, the arrangement 20 of targets is attached to the patient 10. The arrangement is unique with respect to the positions of the targets in three-dimensional space. The targets are typically affixed directly to the patient, but may be attached to a device that is affixed to the patient.

In step 62, target image data are acquired. Depending upon the circumstances, the image data may be captured using any of the three sets of cameras 30 and 32, 38 and 40, or 52 and 54. The image data are manipulated within the image processing circuit 34 in order to calculate position data 64. In the preferred embodiment, the position data are representative of the positions of the individual targets in three-dimensional space. However, for some embodiments of the invention, patient identification is the only concern, so that the calculation of positions of targets relative to each other may be sufficient.

In step 66, a search is conducted to determine if there is a correlation between the position data calculated in step 64 and position data previously recorded within the first memory 46. An identifier circuit 68 may be used to determine whether there is a match between the arrangement of targets on the particular patient 10 and a recorded arrangement. Since the target positioning is unique to each patient, a correlation distinguishes the patient from all other patients. As a result, step 70 identifies the patient or the patient's medical information stored at the second memory 48. The identifier 68 may include a display or other readout device that may be used by an operator to confirm the accuracy of the identification. For example, a computer monitor may present the name of the identified patient 10 and request confirmation. A user-confirmation input device 72, such as a keyboard, can then be used to determine the next step. As shown in FIG. 3, if at step 74 it is determined that the identification is inaccurate, the process returns to step 62 of acquiring image data. On the other hand, if the identification is confirmed, the process is continued.

Returning to step 66, if targets are attached to a patient for a first time, there will be no correlation between the imaged targets and previously recorded target positions. Thus, the calculated position data from step 64 is recorded at step 76 within the first memory 46. Step 78 associates the position data with the particular patient 10.

Returning now to step 74, if the identification of the patient 10 is confirmed, medical information is acquired 80 in the preferred embodiment. The medical information is stored within the second memory 48. In one embodiment, the information is cursory information. For example, a patient tracking component 82 in FIG. 1 may require little more than the name and patient ID number. Patient tracking is utilized to identify a patient during a registration process. For example, if a particular patient arrives for a second session in a multi-session treatment course, the identification process may be used to register the patient and notify relevant personnel that the patient has arrived. Within the station 50 that is used for registration, the targets are attached to the patient and cameras 52 and 54 are used to acquire the image data. Rather than a day-to-day reattachment of the targets, the arrangement may be left in place, if the inconvenience to the patent is not significant. In another embodiment, the tattoos or other markings that are used to reposition the targets may be used for identification purposes, since these markings will also be unique to the patient.

The patient tracking component 82 is particularly useful if the patient is scheduled to visit a number of stations 36 and 50 within a single day. At each station, the arrangement of targets attached to the patient may be imaged and used to track the station-to-station progress of the patient.

While the medical information that is accessed in step 80 may be cursory, the preferred embodiment is one in which the treatment plan of the identified patient 10 is automatically downloaded from the second memory 48 to a session manager 84 of the system. In step 86 of FIG. 3, treatment setup is automated. The automated setup sequence includes manipulating the patient table 12 and the gantry 14 of FIG. 1 to properly position the axis of the radiation beam relative to the treatment area of the patient 10. Moreover, the prescribed radiation field pattern is established by automatically rotating the collimator 16 and manipulating collimator plates to define a geometric shape identified in the treatment plan. In addition, the automated setup sequence includes controlling beam parameters to provide the prescribed settings for beam intensity, exposure time, etc. However, prior to applying the radiation beam, a light source may be activated to form a light field for confirming that the automated sequence has been properly executed. The use of the light field is well known in the art.

By executing an automated setup sequence initiated by patient-specific target identification, the required time for aligning the radiation beam from the gantry 14 with the patient 10 can be significantly reduced. Previously, a radiation device could typically be used for approximately forty patients in one day. By using the position data as a digital fingerprint of the patient, approximately sixty patients may be treated by the radiation device in a single day.

Figure 4:
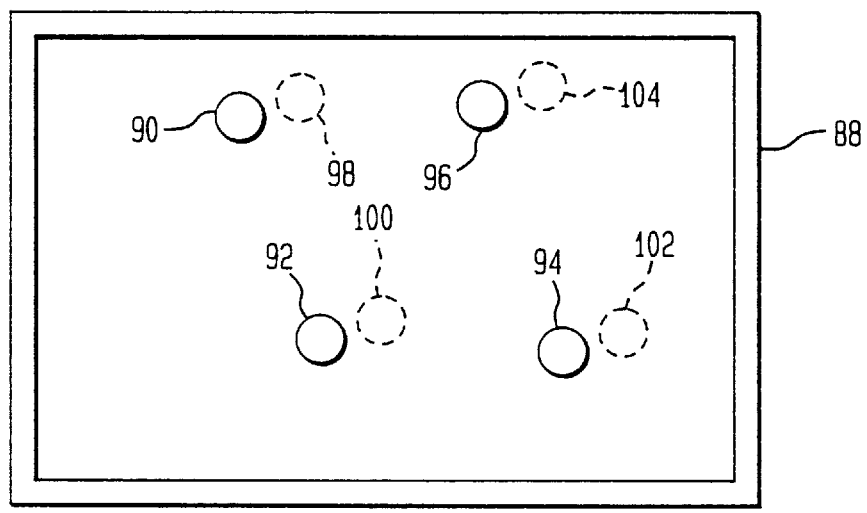
FIG. 4 is a front view of a display of FIG. 1, showing both the actual positions of targets and the desired positions of targets.

Treatment setup time can be reduced even if the process is not fully automated. In one embodiment, the relevant information regarding the patient and the patient's treatment plan are downloaded and displayed for an operator/technologist. Referring now to FIGS. 1 and 4, a display 88 is connected to the session manager 84 to display both the desired positions of the targets 90, 92, 94 and 96 and the actual positions of the targets 98, 100, 102 and 104. The operator/technologist may then reposition the gantry 14 and/or the table 12 to align the two sets of target positions. When the two sets of target positions are properly aligned, the patient 10 will be in the desired position for therapeutic radiation treatment.

I claim:

1. A system for identifying a medical patient among a plurality of patients for localized radiation therapy comprising:

memory means for storing position data representative of arrangements of targets affixed to said plurality of patients for aligning said patients relative to a source of radiation, each arrangement of targets being unique to one of said patients;

imaging means for generating image data responsive to positions of said targets on a particular patient;

processing means, connected to said memory means and said imaging means, for comparing said image data from said imaging means with said position data stored in said memory means; and identification means, responsive to said processing means, for identifying said particular patient based upon detecting a correlation between said image data and said position data.

2. The system of claim 1 wherein said imaging means includes a plurality of cameras and wherein said imaging data is indicative of target positions in three-dimensional space.

3. The system of claim 1 further comprising a plurality of said imaging means and a patient-tracking means for determining location of at least one of said patients in a multi-station medical environment.

4. The system of claim 1 wherein said imaging means has a field of view that is spaced apart from said particular patient when said particular patient is aligned to receive radiation from said source of radiation.

5. The system of claim 4 further comprising a second memory means for storing data indicative of a treatment plan for each of said plurality of patients, said second memory means being responsive to said identification means such that a treatment plan associated with said particular patient is automatically accessed upon identifying said particular patient.

6. The system of claim 1 wherein said imaging means has a field of view that includes said particular patient when said particular patient is aligned to receive radiation from said source of radiation, said system further comprising means for automatically setting up a radiation treatment in response to identification of said particular patient by said identification means.

7. The system of claim 6 further comprising a session manager, connected to said means for automatically setting up a radiation treatment, for manipulating a patient table, a source of radiation and radiation beam parameters.

8. The system of claim 1 further comprising display means, responsive to said identification means, for displaying information relating to said particular patient.

9. The system of claim 1 further comprising input means for requesting and receiving user confirmation of accuracy of said identifying said particular patient by said identification means.

10. The system of claim 1 further comprising said targets, said targets being retroflective members, said imaging means being at least two cameras.

11. A method of processing medical patients for radiation therapy comprising steps of:

affixing targets relative to individual patients for whom radiation therapy is prescribed such that each patient is associated with a unique pattern of positions of said targets;

recording each of said patterns in memory;

establishing a correspondence between each recorded pattern and the patient associated with said recorded pattern;

recording medical information, including recording at least one of a patient radiation treatment plan, a medical history, and patient-location tracking data for each of said patients; and automatically accessing said medical information based upon recognition of one of said patterns, including imaging targets on one of said patients and matching a pattern of said imaged targets with one of said recorded patterns and including accessing said recorded medical information for the patient associated with said matched recorded pattern.

12. The method of claim 11 wherein said step of automatically accessing said medical information comprises a step of accessing setup parameters of a radiation therapy session.

13. The method of claim 11 further comprising a step of downloading said medical information to a session manager of a radiation system and utilizing said medical information to automatically align said patient relative to a source of radiation and to automatically establish a radiation beam geometrical pattern and prescribed radiation beam parameters.

14. The method of claim 13 further comprising a step of displaying said downloaded medical information to an operator of said radiation system.

15. The method of claim 11 further comprising repeating said steps of imaging said targets of said patient and matching said patterns each time that said patient is transferred to a different facility in a multi-facility medical environment, thereby tracking the location of said patient.

16. A method of processing a medical patient for a radiation therapy session comprising steps of:

affixing targets to said patient in a pattern that is unique to said patient;

generating image data of said targets;

determining positions of said targets in three-dimensional space based upon said image data;

comparing said positions to stored position data representative of positions of targets that were affixed to patients during prior radiation therapy sessions; and if a match is detected between said positions of targets affixed to said patient and positions of targets during a prior session, downloading medical information regarding said patient, said medical information including at least one of a patient radiation treatment plan, a medical history, and patient location tracking information, said downloading being based upon an association in memory between said medical information and said positions of targets during said prior session, thereby using said position data as an identifier of said patient.

17. The method of claim 16 wherein said step of downloading said medical information includes downloading setup parameters for said radiation therapy session.

18. The method of claim 17 further comprising automatically establishing a specified patient-to-source relationship specified by said setup parameters, wherein an alignment of said patient relative to a source of therapeutic radiation is determined by said downloaded setup parameters and wherein radiation beam parameters are automatically established.

19. The method of claim 16 further comprising a step of requesting confirmation of accuracy of using said position data as said identifier of said patient.

* * * * *